United States Patent [19]

Sander et al.

[11] Patent Number: 5,628,751

[45] Date of Patent: May 13, 1997

[54] ORTHOPEDIC FASTENER APPLICATOR WITH ROTATIONAL OR LONGITUDINAL DRIVER

[75] Inventors: Thomas W. Sander, Winona Lake, Ind.; Robert Gangnath, Monroe; Daniel R. Lee, New Haven, both of Conn.

[73] Assignee: United States Surgical Corporation, Norwalk, Conn.

[21] Appl. No.: 395,277

[22] Filed: Feb. 27, 1995

Related U.S. Application Data

[63] Continuation of Ser. No. 80,383, Jun. 21, 1993, abandoned.

[51] Int. Cl.$^6$ .................................................. A61B 17/56
[52] U.S. Cl. .................... 606/104; 606/72; 606/86
[58] Field of Search ..................... 606/104, 86, 72, 606/75, 69, 73, 70, 71, 76

[56] References Cited

U.S. PATENT DOCUMENTS

| | | |
|---|---|---|
| 2,941,687 | 6/1960 | Simmons . |
| 4,653,309 | 3/1987 | Hendricks et al. . |
| 4,738,255 | 4/1988 | Goble et al. ............................ 606/86 |
| 4,741,330 | 5/1988 | Hayhurst ................................ 606/86 |
| 4,790,304 | 12/1988 | Rosenberg ............................. 606/72 |
| 4,851,005 | 7/1989 | Hunt et al. ............................. 606/86 |
| 4,903,692 | 2/1990 | Reese .................................... 606/104 |
| 5,046,513 | 9/1991 | Gatturna et al. ...................... 606/72 |
| 5,139,499 | 8/1992 | Small et al. ........................... 606/104 |
| 5,152,765 | 10/1992 | Ross et al. ............................ 606/104 |
| 5,167,665 | 12/1992 | McKinney . |
| 5,207,679 | 5/1993 | Li ......................................... 606/72 |

FOREIGN PATENT DOCUMENTS

| | | |
|---|---|---|
| 0307241 | 9/1988 | European Pat. Off. . |
| 0504915 | 3/1992 | European Pat. Off. . |
| 2225232 | 3/1974 | France . |
| 1457326 | 4/1973 | United Kingdom . |
| WO9204874 | 4/1992 | WIPO . |

Primary Examiner—Robert A. Hafer
Assistant Examiner—Michael O'Neill

[57] ABSTRACT

An instrument for applying an orthopedic fastener activated by a setting pin includes a member for abutting the fastener, a member for grasping the setting pin, and means for moving said members relative to each other. The instrument may be used endoscopically in conjunction with a cannula. An endoscopic drilling member is provided for deployment through the cannula to create a hole for emplacement of the fastener into bone or hard tissue.

14 Claims, 7 Drawing Sheets

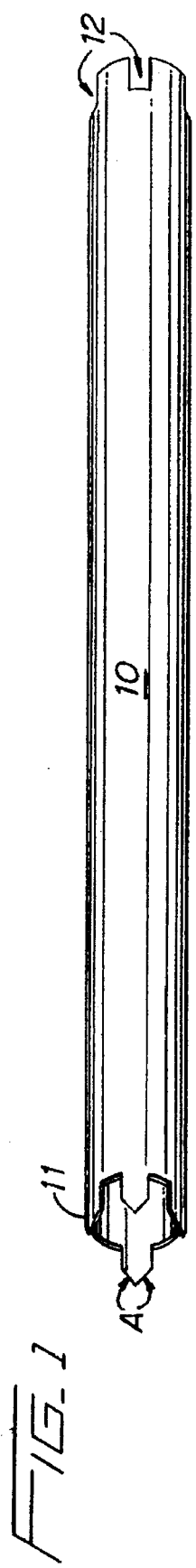
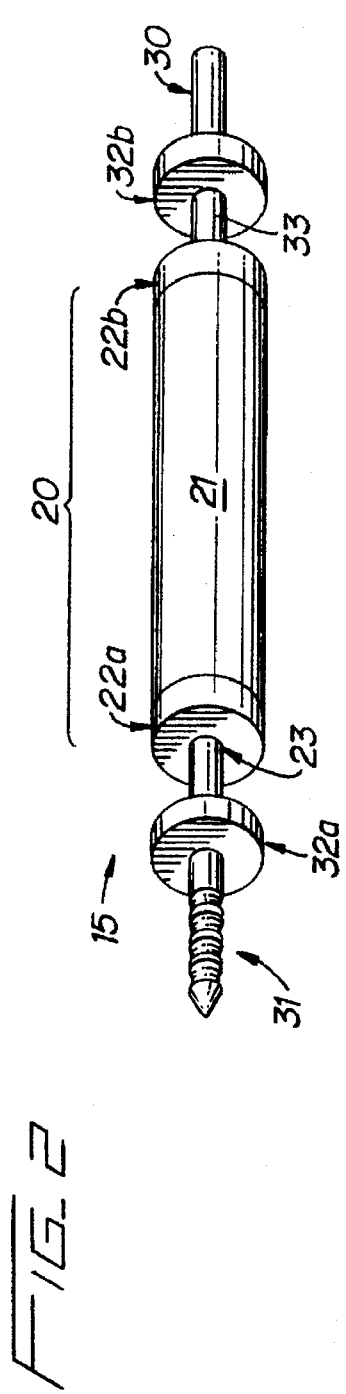
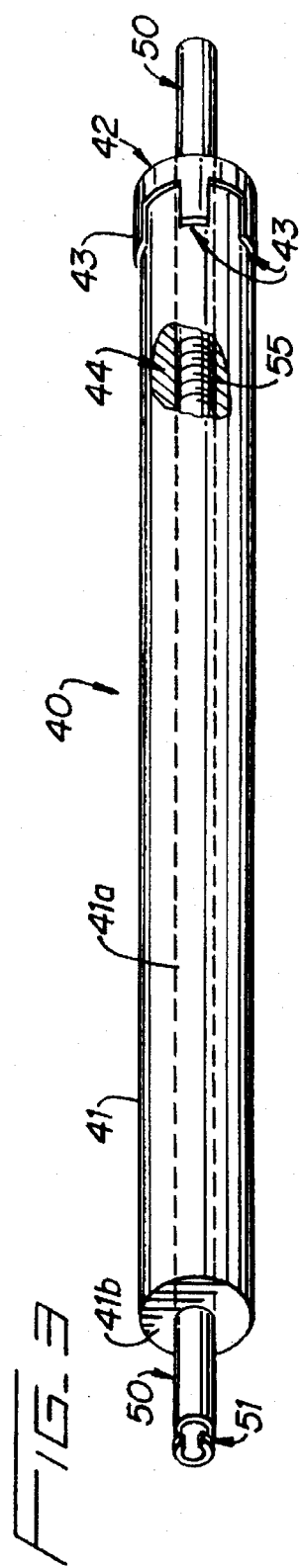
FIG. 1
FIG. 2
FIG. 3

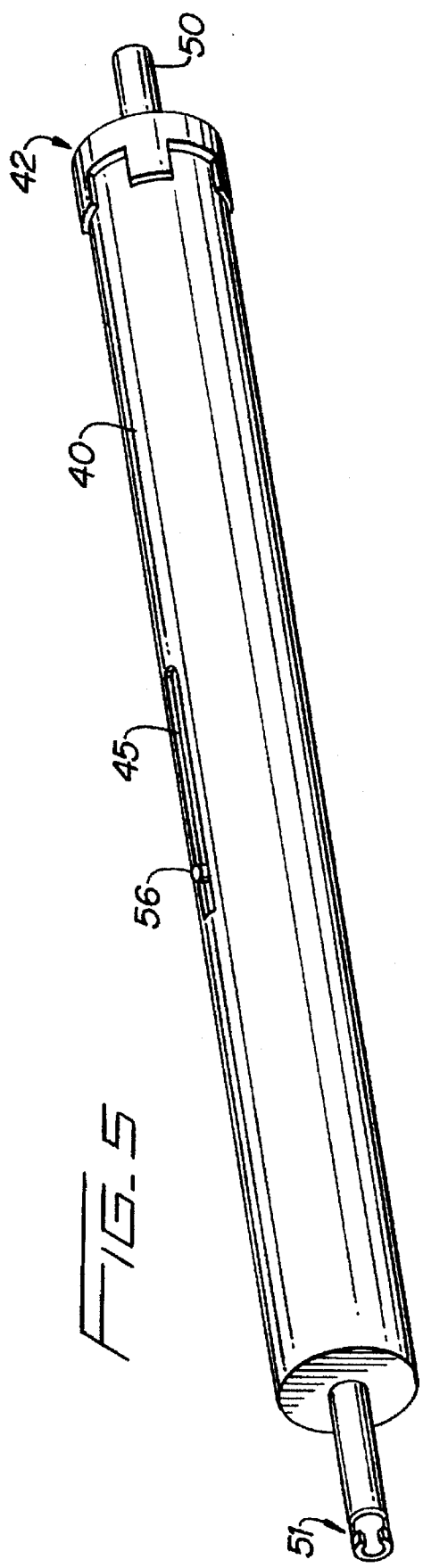
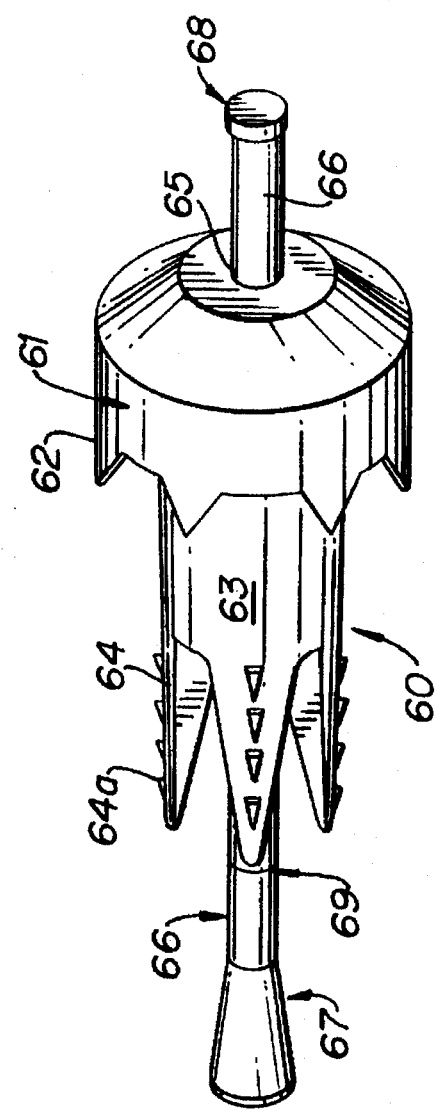

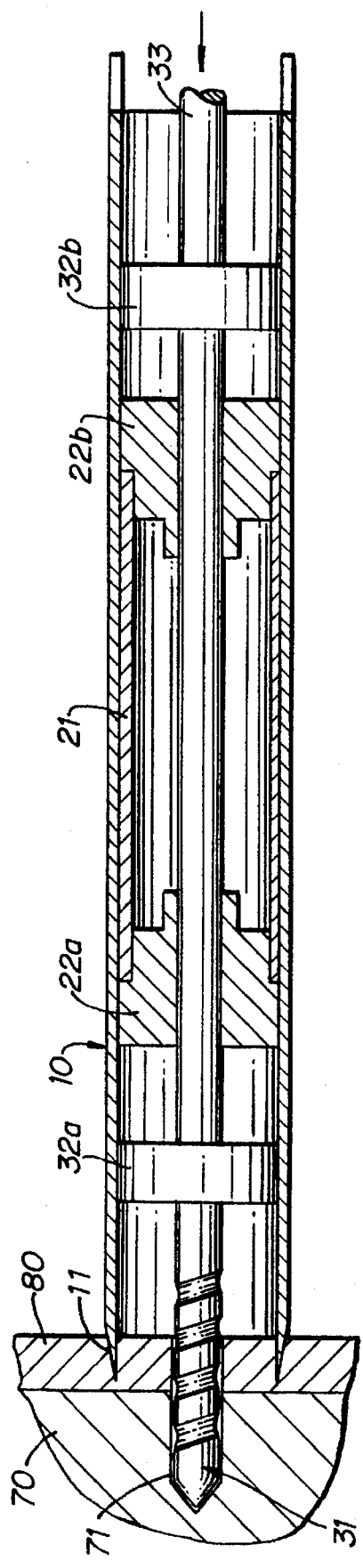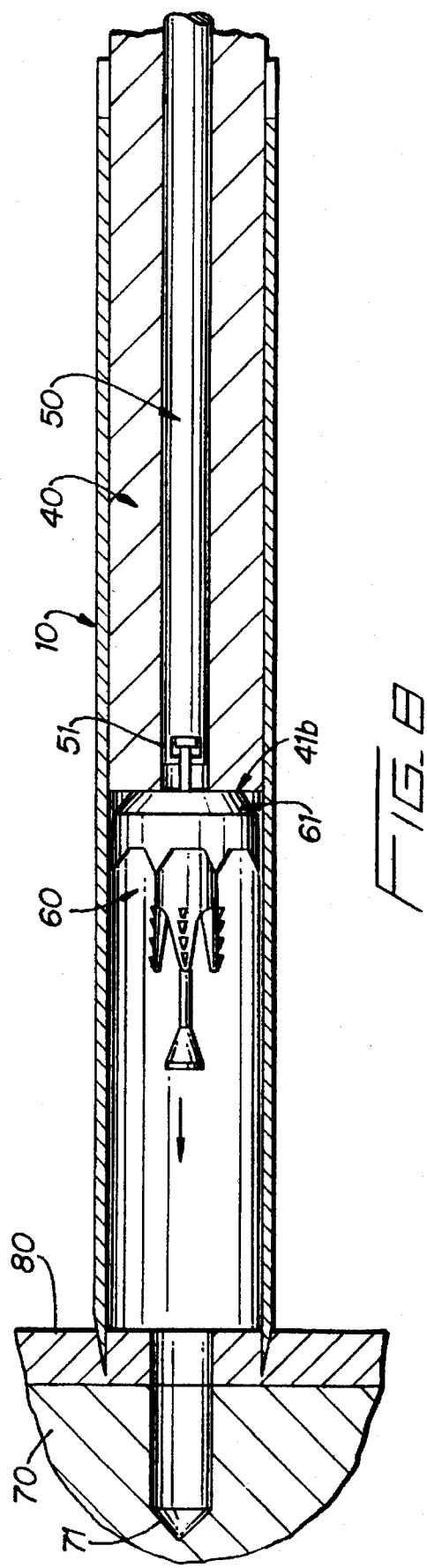

ORTHOPEDIC FASTENER APPLICATOR WITH ROTATIONAL OR LONGITUDINAL DRIVER

This is a continuation of U.S. application Ser. No. 08/080,383 filed Jun. 21, 1993 which is now abandoned.

BACKGROUND OF THE INVENTION

1. Field of the Invention

This invention relates to an insertion tool for applying an orthopedic fastener.

2. Background of the Art

Orthopedic fasteners, i.e. surgical bone fasteners, are known. Also known are surgical fasteners for anchoring soft tissue such as ligament or tendon to bone. Various types of soft tissue anchoring devices are illustrated, for example, in U.S. Pat. Nos. 4,454,875; 4,570,623; 4,927,421; 4,870,975; and 4,927,421.

Bone implantable devices such as those mentioned above are typically made of metal or other hard material. More recently, bone implantable devices have been made from bioabsorbable material, which offers the advantage of gradual transfer of stress back to the bone as the healing proceeds. An example of a bioabsorbable orthopedic fastener for fastening soft tissue to bone is described in U.S. application Ser. No. 07/673,953 filed Mar. 22, 1991 and herein incorporated by reference in its entirety.

Bioabsorbable materials are relatively soft as compared to metals and cannot be self-drilled or impacted into bone. Generally, it is necessary to predrill a hole into the bone and thereafter insert the orthopedic fastener. In particular, the orthopedic fastener described in U.S. application Ser. No. 07/673,953 possesses a pin which, when pulled, biases barbed legs radially outward to anchor the fastener securely within the hole. Up to now, instruments for applying such an orthopedic fastener have not been available.

SUMMARY OF THE INVENTION

An instrument and method for applying a surgical fastener activated by a setting pin is described herein. The instrument includes a fastener abutting means, a grasping means for engaging the setting pin and means for moving the grasping means relative to the fastener abutting means. In one embodiment the instrument may be used endoscopically. A cannula and drill portion are included as part of a kit, the cannula being adapted to receive the drill portion and the applicator. In another embodiment the applicator includes pivotally connected handle members which move the fastener abutment means and the setting pin grasping means to activate the fastener.

BRIEF DESCRIPTION OF THE DRAWINGS

FIG. 1 is a perspective view of the cannula of the present invention.

FIG. 2 is a perspective view of the drill assembly of the present invention.

FIG. 3 is a perspective view of the fastener manipulator assembly of the present invention.

FIG. 5 is a perspective view of an alternative embodiment of the fastener manipulator assembly.

FIG. 6 is a perspective view of a fastener.

FIGS. 7 to 10 are partly sectional views illustrating the fastener applicator of the present invention in use for implanting an orthopedic fastener.

DETAILED DESCRIPTION OF PREFERRED EMBODIMENTS

Figure 4:
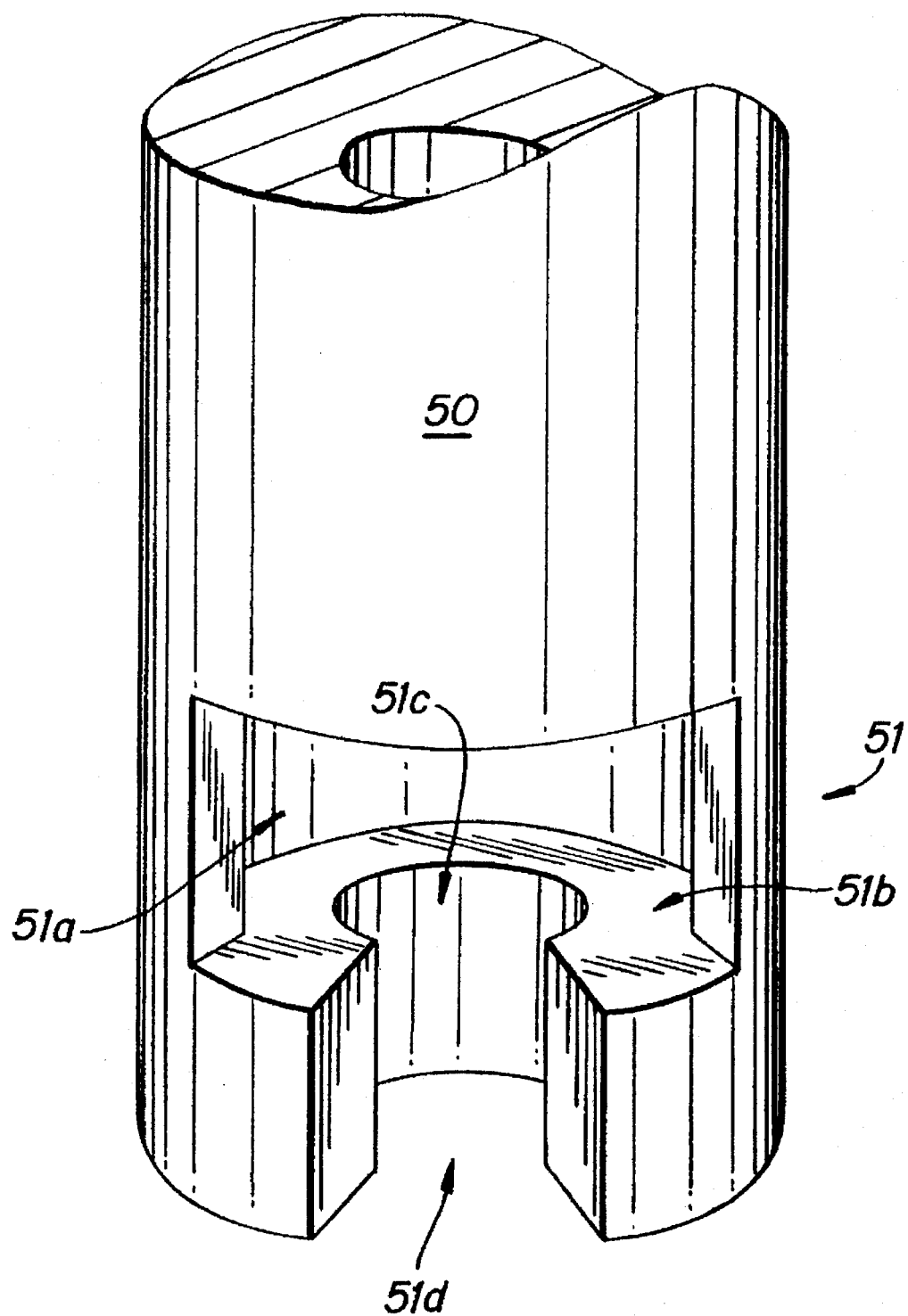
FIG. 4 is a perspective view of the fastener grasping means of the fastener manipulator assembly.

Referring to FIGS. 1, 2, and 3, the orthopedic fastener applicator kit of the present invention includes a cannula 10, a drill assembly 15, and a fastener manipulator assembly 40. The fasteners intended to be manipulated and applied by the present invention have been described in U.S. application Ser. No. 07/673,953, as indicated above. An illustration of this type of fastener is presented in FIG. 6.

Briefly, fastener 60 is activated by a proximally moving setting pin and includes a proximal head portion 61 with distally pointing barbs 62 for securing soft tissue (e.g. ligament, tendon, etc.). A base portion 63 includes distally projecting and radially expandable legs 64 having radially outward pointing barbs 64a. A setting pin 66 is slidably disposed through aperture 65 which extends axially through the fastener 60. Setting pin 66 has a flared distal end 67, preferably a circumferential break away notch 69, and optionally a relatively wider diameter head 68 to facilitate the grasping and pulling of the pin 66 by an instrument. When the setting pin 66 is pulled proximally, flared end 67 biases legs 64 radially outward to anchor base 63 of the fastener in a hole predrilled into bone. The setting pin 66 snaps apart at notch 69, which is located proximally of legs 24 when the setting pin is pulled to its maximum extent, so as not to leave any portion of the pin projecting therefrom. Fastener 60 is preferably fabricated from a bioabsorbable material such as homopolymers and copolymers of glycolide, lactide, p-dioxanone, and caprolactone.

This instrument of the present invention may be used endoscopically. An endoscopic operation is one in which a surgical procedure is carried out in the interior of a human (or animal) body by means of instrumentation for operating or viewing deployed through one or more tubes, the functional portion of the instrumentation being manipulated or controlled from outside the body. The initial opening in the body tissue to allow passage of the endoscopic tube to the interior of the body can be a natural passageway of the body (e.g. bronchial tubes), or it can be a puncture produced by an instrument such as a trocar. Because the endoscopic tubes, instrumentation, and any required puncture are relatively narrow, endoscopic surgery is less invasive and causes much less trauma to the patient as compared with surgery in which the surgeon is required to cut open large areas of body tissue.

Referring to FIGS. 1, 2, and 3, cannula 10 provides a tubular guideway and supports the operating instrumentation described below. It is preferably made of a surgically suitable metal, such as stainless steel. Distally pointing barbs 11 are located at the distal end of the cannula 10, and they facilitate the grasping, temporary holding and placement of the soft tissue intended to be secured to bone. Angle A of the point of the barb 11 is preferable from about 10 degrees to about 30 degrees, and more preferably from about 15 degrees to about 25 degrees. The outer diameter of the cannula 10 preferably ranges from about 0.28 inches to about 0.42 inches. The inner diameter of the cannula preferably ranges from about 0.27 inches to about 0.39 inches. Clearly, cannulas of other dimensions can be utilized with the present invention. The cannula preferably can be from about 2 to about 6 inches in length. The proximal end of cannula 10 includes notches 12 for receiving corresponding projections 43 of the end cap 42, described below.

FIG. 2 illustrates a drill assembly 15 which includes a guide tube portion 20 and a drill portion 30. The guide tube portion 20 includes hollow cylinder 21 having end plugs 22a and 22b, each having an axial bore 23 of substantially the same diameter. Drill portion 30 includes axial drill shaft 33 extending longitudinally through the axial bores 23 so as to be centrally aligned through the guide tube 20. End plugs 22a and 22b serve as bearings for shaft 33. The shaft is rotatable and longitudinally movable with respect to the guide tube 20. The outer diameter of the drill shaft 33 is substantially equal to the diameter of the bores 23 so as to reduce deviation of the drill shaft 23 from precise alignment along the central longitudinal axis of the instrument. At its distal end, shaft 23 possesses a drill bit 31 and, at positions respectively distal and proximal to the guide tube portion 20, the drill portion 30 possesses stops 32a and 32b fixedly attached to shaft 33 to limit the degree of longitudinal movement of the drill portion 30 relative to the guide assembly 20. Precise alignment of the drill along the central longitudinal axis of the instrument is facilitated by close tolerances between the respective parts of the instrument. Thus, the outer diameter of guide tube 20 as well as the outer diameters of stops 32a and 32b are substantially equal to the inner diameter of the cannula 10. The end plugs 22a and 22b, and stops 32a and 32b support the drill shaft 33 and maintain the drill 30 in axial alignment within drill assembly 15 and also help to suppress bending of the drill 30, thereby maintaining its rectilinearity.

The cylindrical tube 21 is preferably fabricated from a surgically suitable metal such as stainless steel. The end plugs 22a and 22b, which serve as bearings, are preferably fabricated from polymeric material having suitable strength, abrasion and wear resistance, and non-stick characteristics. For example, a material suitable for use in fabricating such bearings is DELRIN® AF, available from E. I. DuPont de Nemours, & Co., Inc. of Parkersburg, W. Va., which comprises an acetal polymeric resin containing fibers of polytetrafluoroethylene. The drill portion can be fabricated from any metal alloy suitable for drilling in surgical applications.

Referring now to FIG. 3, fastener manipulator assembly 40 includes cylindrical member 41 having an axial bore 41a through which manipulator rod 50 is movably disposed and a distal surface 41b, which is a fastener abutting means for abutting the proximal end surface of the fastener head. An end cap 42 is located at the proximal end of member 41 and possesses distally extending projections 43 for engaging corresponding notches 12 of the cannula. Cylindrical member 41 is adapted to slide into cannula 10 and possesses an outer diameter substantially equal to the inner diameter of the cannula 10.

The term "drive means" as used herein refers to a means such as manipulator rod 50 for proximally moving a grasping means relative to the fastener abutting means. Manipulator rod 50 possesses a setting pin grasping means 51 at its distal end, and optionally a threaded portion 55 adapted to screw into a corresponding tapped portion 44 in the inside surface of the bore 41a. An embodiment of the setting pin grasping means 51 is illustrated in FIG. 4 and includes an opening 51a adapted to allow entry and positioning of the head 68 of setting pin 66. Grasping means 51 also includes a wedge shaped slot 51d, longitudinally extending aperture 51c, and shelf 51b. The head 68 of pin 66 is inserted by sliding pin 66 through slot 51d such that the shaft of pin 66 extends through aperture 51c and the head 68 is located inside opening 51a and rests on shelf 51b. When the manipulator rod 50 is moved proximally the pin is thereby pulled from the fastener.

Proximal or distal movement of the manipulator rod 50 shown in FIG. 3 is achieved by rotating the rod 50 relative to the cylindrical member 41 so as to screw rod 50 into or out of aperture 41a.

In another embodiment, as shown in FIG. 5, the manipulator rod 50 has no threads and slides longitudinally along the axis of the instrument without the necessity of rotating. Optionally, a longitudinally oriented elongated slot 45 is included in member 41. A peg 56 is attached to rod 50 and projects radially outward therefrom into slot 45. The longitudinal motion of the rod 50 within member 41 is thereby limited to the length of the slot.

Referring now to FIGS. 7 to 10, operation of the apparatus is carded out as follows:

The cannula 10 is positioned on the bone 70 at the location where the surgeon intends to implant the orthopedic fastener. The barbs 11 can be used to pick up and move soft tissue 80 to the desired location.

The drill assembly 15 is inserted into the cannula 10 and advanced distally, as shown in FIG. 7. The drill assembly 30 is rotated by means of any suitable type drill motor (not shown) attached to the proximal end of the shaft 33 to advance the drill assembly distally. A hole 71 is thereby created in the bone mass 70.

Figure 9:
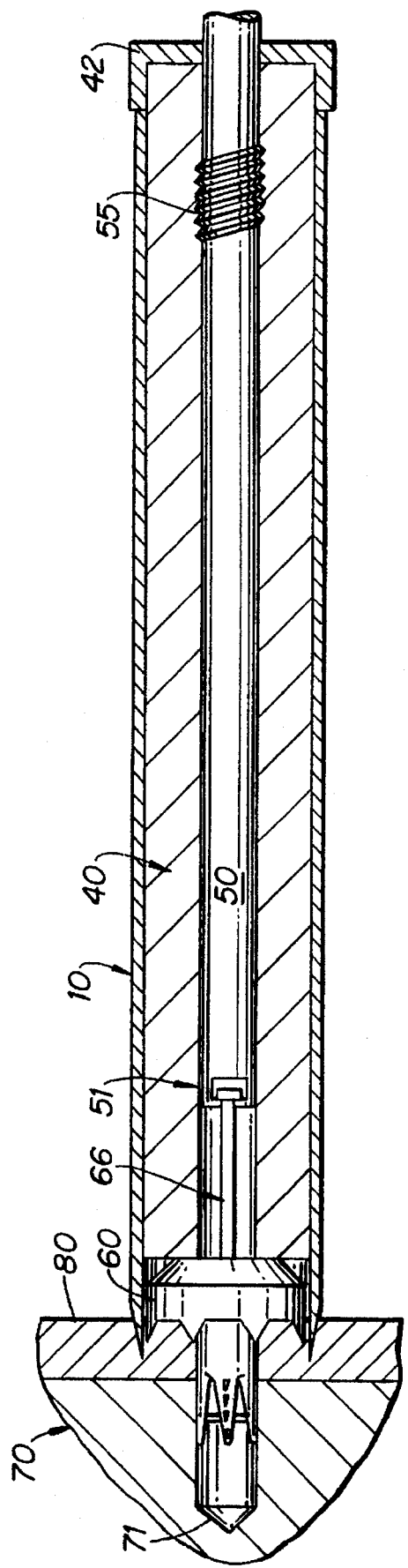
Figure 10:
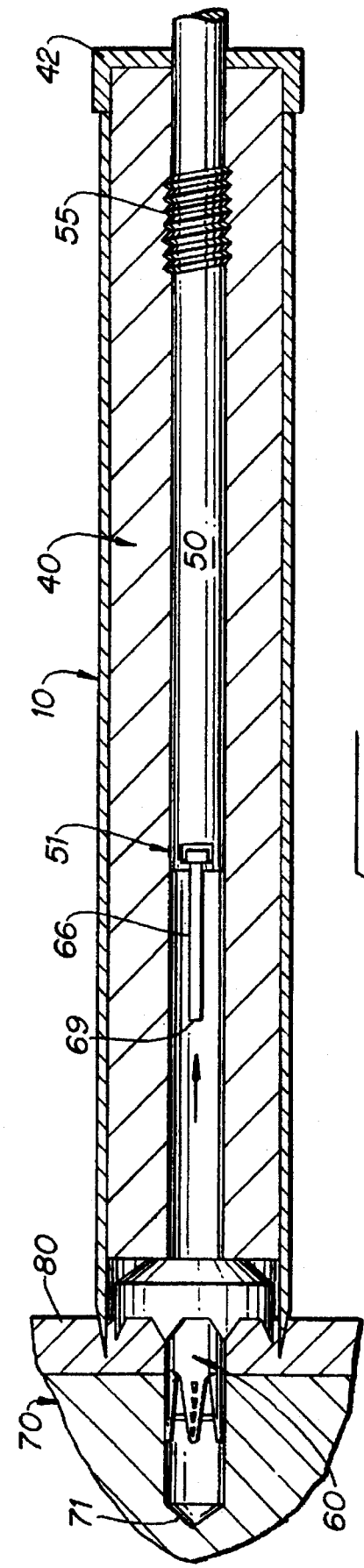

After the hole has been completed, the drill assembly 15 is removed from the cannula 10. A fastener 60 is connected to the fastener manipulator assembly 40 by inserting the setting pin head 68 of a fastener into the opening 51a of the grasping means 51. Slight retraction of rod 50 will straighten the fastener 60. The fastener manipulator assembly is then inserted into the cannula 10 and moved distally to insert the fastener into the prepared hole 71, as shown in FIG. 8. The cylindrical member 41 and fastener manipulator rod 50 are adjusted either by turning or sliding rod 50 in accordance with the embodiments as described above so as to position the distal end 41b of the cylindrical member 41 in abutment with the proximal side of the fastener head 61, as shown in FIG. 9. After the fastener 60 has been suitably positioned within hole 71 the manipulator rod 50 is withdrawn proximally either by turning or sliding, thereby pulling setting pin 66, as shown in FIG. 10. The flared portion 67 of the pin biases legs 64 outwardly to anchor the pin 66 in hole 71. With sufficient pulling force, pin 66 snaps apart at notch 69. The cannula 10 and manipulator assembly 40 may then be removed.

Figure 11:
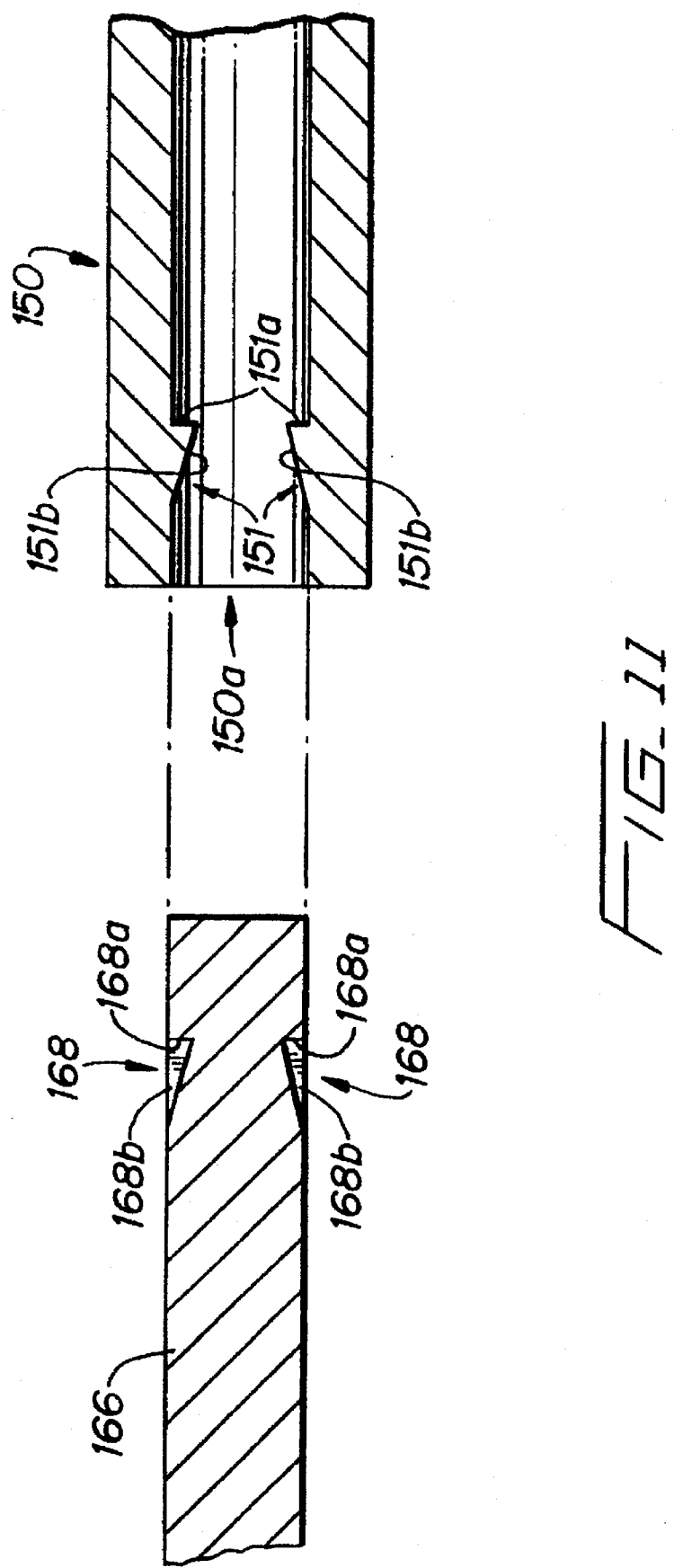
FIG. 11 is a sectional view of an alternative embodiment of the setting pin and the grasping means.

An alternative configuration of the setting pin and setting pin grasping means is illustrated in FIG. 11. As mentioned above, the wider diameter head portion 68 of the setting pin is optional. FIG. 11 illustrates a setting pin 166 which possesses notches 168 instead of a wider diameter head portion. The notches 168 each include a proximal abutment surface 168a and preferably one, and more preferably two, side abutment surfaces. The manipulator rod 150 has an inner bore 150a adapted to receive the proximal end of setting pin 166. Detents 151 are adapted to snap fit into notches 168 when the setting pin 166 is inserted into the bore 150a of the manipulator rod. Proximally facing abutment surfaces 151a of the manipulator rod are adapted to abut the proximal abutment surfaces 168a of the notches. Thus, after engagement of the manipulator rod 150 and the setting pin 166, proximal movement of the manipulator rod 150 causes proximal movement of the setting pin 166. The detents 151 each have a sloping distal surface 151b to facilitate entry of the setting pin. The detents 151 can be of integral construction with the manipulator rod 150. The manipulator rod should then have sufficient resiliency to open the diameter of its bore 150a sufficiently to permit entry of the setting pin 166 and snap locking engagement of the manipulator rod 150 and the setting pin 166. Side abutment surfaces 168b facilitate rotation of the setting pin 166 by manipulator rod 150 when the manipulator rod 150 is moved by screw motion, as discussed above.

Figure 12:
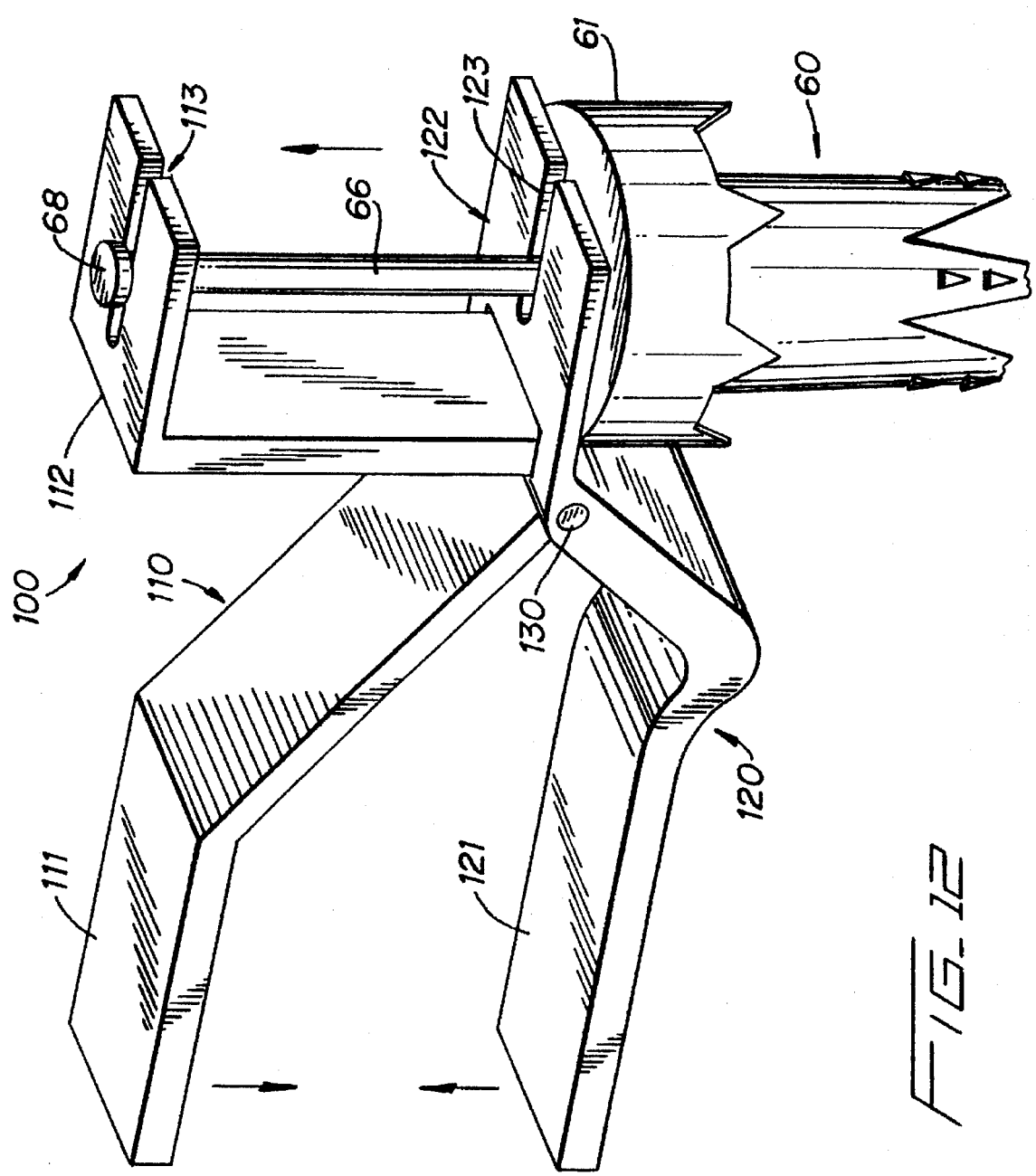
FIG. 12 is a perspective view of an alternative embodiment of applicator of the present invention.

The embodiment of the present invention presented above can be used endoscopically. In some surgical applications, non-endoscopic type applicators may be used. FIG. 12 illustrates an alternative, non-endoscopic embodiment of the present invention.

Fastener applicator 100 comprises members 110 and 120 pivotally connected by pin 130. Each member has a handle portion 111 and 121, respectively, and a fastener grasping portion 112 and 122, respectively. Notches 113 and 123 in fastener grasping portions 112 and 122 allow engagement with an orthopedic fastener, the fastener setting pin 66 being disposed in notches 123 and 113 as illustrated. When the handles 111 and 112 are squeezed, fastener grasping portions 112 and 122 are splayed further apart. Fastener grasping portion 112 abuts setting pin head 68, and fastener grasping portion 122 abuts fastener head 61. Hence, when the fastener grasping portions 112 and 122 are splayed further apart, setting pin 66 is pulled proximally out of the fastener 60 and the fastener is activated as described above.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. An endoscopic apparatus for applying a surgical fastener activated by a proximally moving setting pin, which comprises:
   a) fastener abutting means for abutting a surgical fastener, said fastener abutting means comprising an elongated tube having an axial bore and a distal fastener abutting surface;
   b) grasping means for engaging a proximal portion of the setting pin, said grasping means being movable with respect to said fastener abutting means; and
   c) drive means for proximally moving said grasping means relative to said fastener abutting means, said drive means comprising an elongated cylindrical member movably disposed within the axial bore of the fastener abutting means, and further including a threaded portion for engaging a tipped portion of the axial bore of the fastener abutting means whereby said drive means is moved relative to the fastener abutting means by a screw motion.

2. An endoscopic apparatus for applying a surgical fastener activated by a proximally moving setting pin, which comprises:
   a) a fastener abutting means for abutting a surgical fastener, said fastener abutting means comprising an elongated tube having an axial bore and a distal fastener abutting surface and an elongated longitudinally oriented notch;
   b) grasping means for engaging a proximal portion of the setting pin, said grasping means being movable with respect to said fastener abutting means; and
   c) drive means for proximally moving said grasping means relative to said fastener abutting means, said drive means comprising an elongated cylindrical member movably disposed within the axial bore of the fastener abutting means, and further including a peg extending into said elongated notch of said fastener abutting means.

3. An apparatus for orthopedic fixation, which comprises:
   a) at least one orthopedic surgical fastener activated by a proximally movable setting pin having proximal and distal end portions; and,
   b) a fastener applicator for containing and distally applying said orthopedic surgical fastener, said fastener applicator including
      i) fastener abutting means for abutting the orthopedic surgical fastener, wherein said fastener abutting means includes an elongated tube having an axial bore and a distal fastener abutting surface, said axial bore having a tapped portion;
      ii) grasping means for engaging the proximal end portion of the setting pin, said grasping means being movable with respect to said fastener abutting means; and
      iii) drive means for proximally moving said grasping means relative to said fastener abutting means, wherein said drive means includes an elongated cylindrical member movably disposed within the axial bore of the fastener abutting means, and a threaded portion for engaging the tapped portion of the axial bore of the fastener abutting means, said drive means being movable relative to the fastener abutting means by a screw motion.

4. The apparatus of claim 3, wherein said apparatus is endoscopic.

5. The apparatus of claim 4, wherein the fastener setting pin includes a proximal relatively wider diameter head portion and the grasping means comprises a surface for engaging said head portion.

6. The apparatus of claim 4, wherein said fastener setting pin includes at least one notch and the grasping means includes at least one detent configured and dimensioned to engage said notch.

7. The apparatus of claim 6, wherein said grasping means is located at the distal end of said drive means.

8. The apparatus of claim 3, wherein said fastener abutting means includes an elongated, longitudinally oriented notch, and said drive means possesses a peg extending into the elongated notch.

9. The apparatus of claim 4, further including a cannula, the fastener abutting means being slidably movable within the axial bore of the cannula.

10. The apparatus of claim 9, wherein said cannula possesses at least one barb at its distal end.

11. The apparatus of claim 9, wherein the cannula possesses at least one notch at its proximal end and the fastener abutting means possesses a proximal end cap having at least one distal pointing projection for engaging said at least one notch.

12. The apparatus of claim 3, wherein said fastener abutting means comprises a member having a fastener abutting surface and a notch for receiving the setting pin of the fastener.

13. The apparatus of claim 12, wherein the fastener setting pin includes a proximal relatively wider diameter head portion and the grasping means comprises a surface for engaging said head portion and a notch for receiving said setting pin.

14. The combination of claim 13 wherein said fastener abutting means and grasping means are each mounted to a respective handle member, said handle member being pivotally connected to each other.

* * * * *